Figure 1:
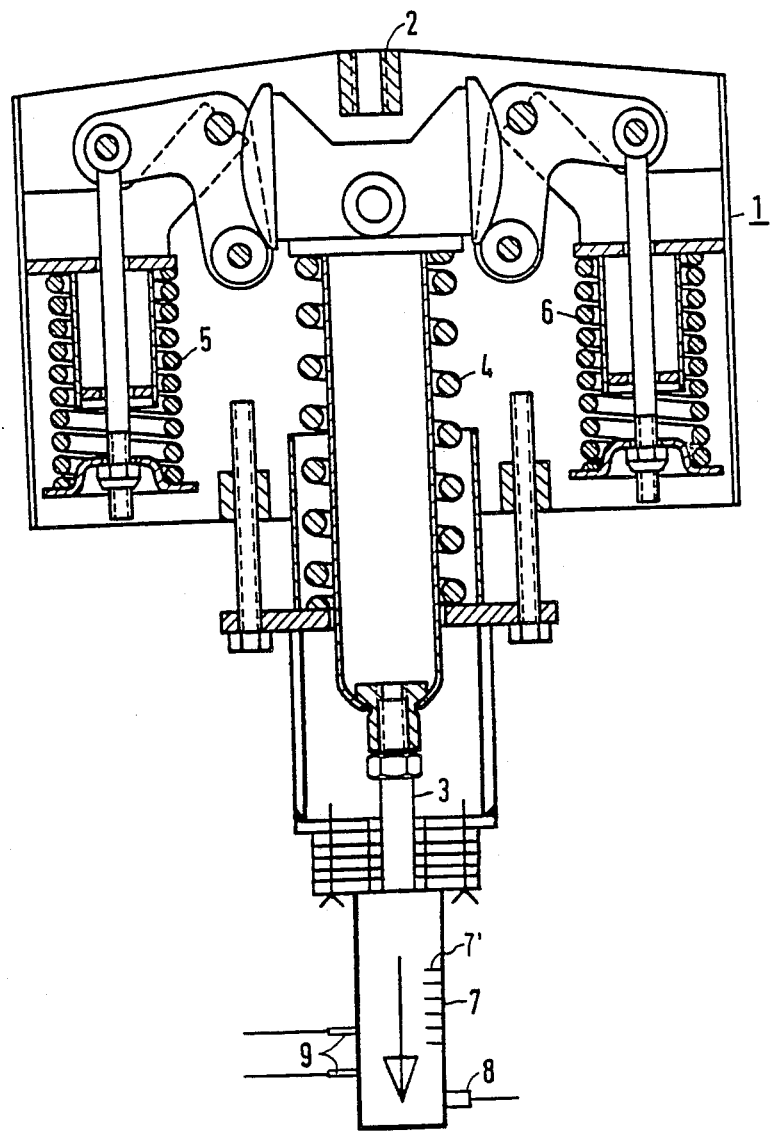

United States Patent [19]

Pospischil et al.

[11] Patent Number: 4,862,742

[45] Date of Patent: Sep. 5, 1989

[54] METHOD AND APPARATUS FOR FUNCTIONAL TESTING OF A SUSPENSION DEVICE FOR A LOAD

[75] Inventors: Werner Pospischil, Roedermark; Guenter Hartwig, Hanau, both of Fed. Rep. of Germany

[73] Assignee: Siemens Aktiengesellschaft, Munich, Fed. Rep. of Germany

[21] Appl. No.: 219,084

[22] Filed: Jul. 14, 1988

[30] Foreign Application Priority Data

Jul. 14, 1987 [DE] Fed. Rep. of Germany ....... 3723242

[51] Int. Cl.$^4$ ............................ G01L 1/04; G01N 3/26
[52] U.S. Cl. .......................................... 73/161; 73/789; 248/58; 248/317; 248/542
[58] Field of Search .................... 73/161, 789; 248/58, 248/542, 317, 343

[56] References Cited

U.S. PATENT DOCUMENTS

| | | | |
|---|---|---|---|
| 3,102,706 | 9/1963 | Goldsmith | 248/542 |
| 3,285,065 | 11/1966 | Ragen et al. | 73/161 |
| 3,588,010 | 6/1971 | Liesegang | 248/542 |
| 3,638,486 | 2/1972 | Lambert | 73/161 |
| 3,665,758 | 5/1972 | Tiller | 73/161 |
| 3,881,348 | 5/1975 | Morton | 73/161 |
| 4,157,033 | 6/1979 | Shereda et al. | 73/161 |
| 4,175,431 | 11/1979 | DeTournay | 73/161 |
| 4,186,594 | 2/1980 | Mitchell | 73/161 |
| 4,714,230 | 12/1987 | Huang | 248/343 |

FOREIGN PATENT DOCUMENTS

| | | | |
|---|---|---|---|
| 637631 | 12/1978 | U.S.S.R. | 73/161 |
| 700802 | 11/1979 | U.S.S.R. | 73/161 |

Primary Examiner—William A. Cuchlinski, Jr.
Assistant Examiner—Diego F. F. Gutierrez
Attorney, Agent, or Firm—Herbert L. Lerner; Laurence A. Greenberg

[57] ABSTRACT

A method and an apparatus for functional testing of a suspension device for a load, is used in combination with a suspension device such as a spring hanger or a constant support hanger holding a pipe run on a building structure and having at least one mechanical spring. The load is released from the suspension device and held with other devices. A hydraulic device is connected to the suspension device to be tested instead of the load for stretching the spring of the suspension device. The pressure necessary for stretching the spring and therefore the spring constant of the spring based on the operating travel of the spring, are ascertained and recorded with a pressure pickup and a recorder connected to the hydraulic device.

8 Claims, 2 Drawing Sheets

METHOD AND APPARATUS FOR FUNCTIONAL TESTING OF A SUSPENSION DEVICE FOR A LOAD

The invention relates to a method and an apparatus for functional testing of a suspension device for a load, especially a spring hanger or a constant support hanger for holding a pipe run or pipeline on a building structure, the suspension device being equipped with at least one mechanical spring.

Spring hangers and constant support hangers are generally known. They are used, for example, in power plants where they serve to secure pipe runs on building structures. Vibration in the pipe runs is damped by the mechanical springs used in the prior art suspension devices.

After a long service time, the dampening properties of the conventional suspension devices may worsen. The suspension devices which are used must therefore be tested at certain time intervals.

Previously, the usual procedure was to remove the suspension devices to be tested for testing. The functional testing is done on a test stand intended for this purpose Given the great number of suspension devices that must be tested in a power plant, a considerable expenditure of time and money is involved in removing them, transporting them to the test stand, testing them, transporting them back again and reinstalling them.

It is accordingly an object of the invention to provide a method and apparatus for functional testing of a suspension device for a load, which overcomes the hereinafore-mentioned disadvantages of the heretofore-known methods and devices of this general type, which can be performed without removal of the device to be tested and which therefore can be performed very quickly and at favorable cost, with high reliability.

With the foregoing and other objects in view there is provided, in accordance with the invention, in combination with a suspension device such as a spring hanger or a constant support hanger holding a pipe run on a building structure and having at least one mechanical spring, a method for functional testing of the suspension device for a load, which comprises releasing the load from the suspension device, holding the load with other devices, connecting a hydraulic device instead of the load to the suspension device to be tested for stretching the spring of the suspension device, and ascertaining and recording the pressure necessary for stretching the spring and therefore the spring constant of the spring based on the operating travel of the spring, with a pressure pickup and a recorder connected to the hydraulic device The hydraulic device stretches the spring as if by a suspended load. The stretching takes place in increments over the entire operational travel of the spring, which for instance is 60 mm long. After each stretching increment, for example at intervals of 10 mm, the instantaneous pressure required in the hydraulic device to stretch the spring is measured by a pressuring pickup connected to the hydraulic device. A recorder combined with an evaluation unit determines the course of the spring constant of the spring over the operating travel from the measured values and records this course.

The spring constant corresponds to the force upon a spring that is necessary in order to stretch the spring by a certain travel distance. According to the invention, the force is determined from the measured pressure in the hydraulic device. The precise instantaneous stretching of the spring is determined from the position of the movable part of the hydraulic device at measurement points disposed on the housing of the hydraulic device.

The advantage attained with the invention is that suspension devices and in particular spring hangers and constant support hangers can be tested for functional ability where they are installed, without being removed. If a very great number of such suspension devices is to be tested, for instance those used in a power plant for holding pipe runs, then this testing can be performed particularly quickly and economically with the method according to the invention. The method according to the invention is particularly suitable for the functional testing of the spring hangers and constant support hangers holding the pipe runs in nuclear power plants. A very great number of suspension devices can be tested quickly and reliably in such a case.

With the objects of the invention in view, there is also provided, in combination with a suspension device holding a pipe run on a building structure and having at least one mechanical spring, an apparatus for functional testing of the suspension device for a load, comprising a hydraulic device instead of the load connected to the suspension device to be tested for stretching the spring of the suspension device, the hydraulic device having a plurality of measuring points, and a pressure pickup and a recorder connected to the hydraulic device for determining and recording the pressure necessary for stretching the spring and therefore the spring constant of the spring in the suspension device based on the operating travel of the spring.

In accordance with another feature of the invention, there is provided a hydraulic pump connected to the hydraulic device.

Disposed in the hydraulic device is a piston that can be connected to the spring of the suspension device. This piston is acted upon by the medium of the hydraulic device and is displaced thereby, which stretches the spring. Since the connection between the piston and the spring is rigid, the displacement travel of the piston that can be read from the measurement points corresponds to the stretching travel of the spring. Once the piston has attained a measurement point, the pressure in the piston is determined by the pressure pickup. The spring constant of the spring and the suspension device can be determined from the determination of the pressure in the piston and the stretching travel. If the spring constant is unchanged from its original value, then the suspension device is reliably functional.

The advantage attained with the apparatus according to the invention as described is that suspension devices can be tested without being removed.

In particular, the invention enables both quick and reliable functional testing to be performed.

For example, in accordance with a further feature of the invention, the suspension device to be tested has a housing, and there is provided a clamping device connected to the suspension device to be tested and supported on the housing of the suspension device, the hydraulic cylinder having a housing held in the clamping device, a device connected to the hydraulic cylinder for holding a load with the suspension device, a force measuring instrument disposed between the device for holding a load and the hydraulic cylinder, an evaluation unit electrically connected to the force measuring instrument, and a travel pickup for measuring the displacement travel being connected to the clamping device, connected to the device for holding a load and electrically connected to the evaluation unit. The device for holding a load is part of the suspension device.

The apparatus described above is particularly suitable for performing the method according to the invention.

For example, in accordance with an added feature of the invention, there is provided a conical adaptor washer disposed between the housing of the suspension device to be tested and the clamping device. Various housing diameters of the suspension device and clamping device can be compensated for in this way.

In accordance with a concomitant feature of the invention, there is provided a threaded sleeve mechanically connecting the device for holding a load to the hydraulic cylinder. In this way, the apparatus according to the invention for performing the testing method can be used with variously equipped suspension devices by replacing the threaded sleeve.

The procedure for testing a suspension device according to the invention, is as follows:

After the load is removed, a connection is established between the hydraulic cylinder and the suspension device, through suitable threaded sleeves. The hydraulic cylinder is supported through the clamping device, which is mounted between the hydraulic cylinder and the housing of the suspension device, on the housing of the suspension device. Various diameters of the housing are compensated for with a conical adaptor washer, which is placed between the housing of the suspension device and the housing of the clamping device. After the attachment, the travel pickup is connected. The travel pickup is installed firmly on the clamping device. A force measuring instrument or box is disposed between the hydraulic cylinder and the threaded sleeve. Before measurement begins, the evaluation unit which is connected to measuring amplifiers, is calibrated. Next, the characteristic curve of the mechanical spring of the suspension device is ascertained. To this end, the spring is stretched with the hydraulic cylinder, while measured values of the force meter and travel pickup are evaluated.

The advantage attained with the method and apparatus for performing the method according to the invention is that a deviation of the spring constant from the set-point value can be determined quickly and reliably. Moreover, the cold load and hot load of the spring can also be ascertained, and regulated.

With the method and apparatus according to the invention, it becomes possible to achieve a recognition of abnormalities in the characteristic curve perhaps in the hysteresis of the spring that would impair the function of the suspension device if a very great strain occurs, for example in an earthquake which causes great dynamic travel.

Other features which are considered as characteristic for the invention are set forth in the appended claims.

Although the invention is illustrated and described herein as embodied in a method and apparatus for functional testing of a suspension device for a load, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

Figure 2:
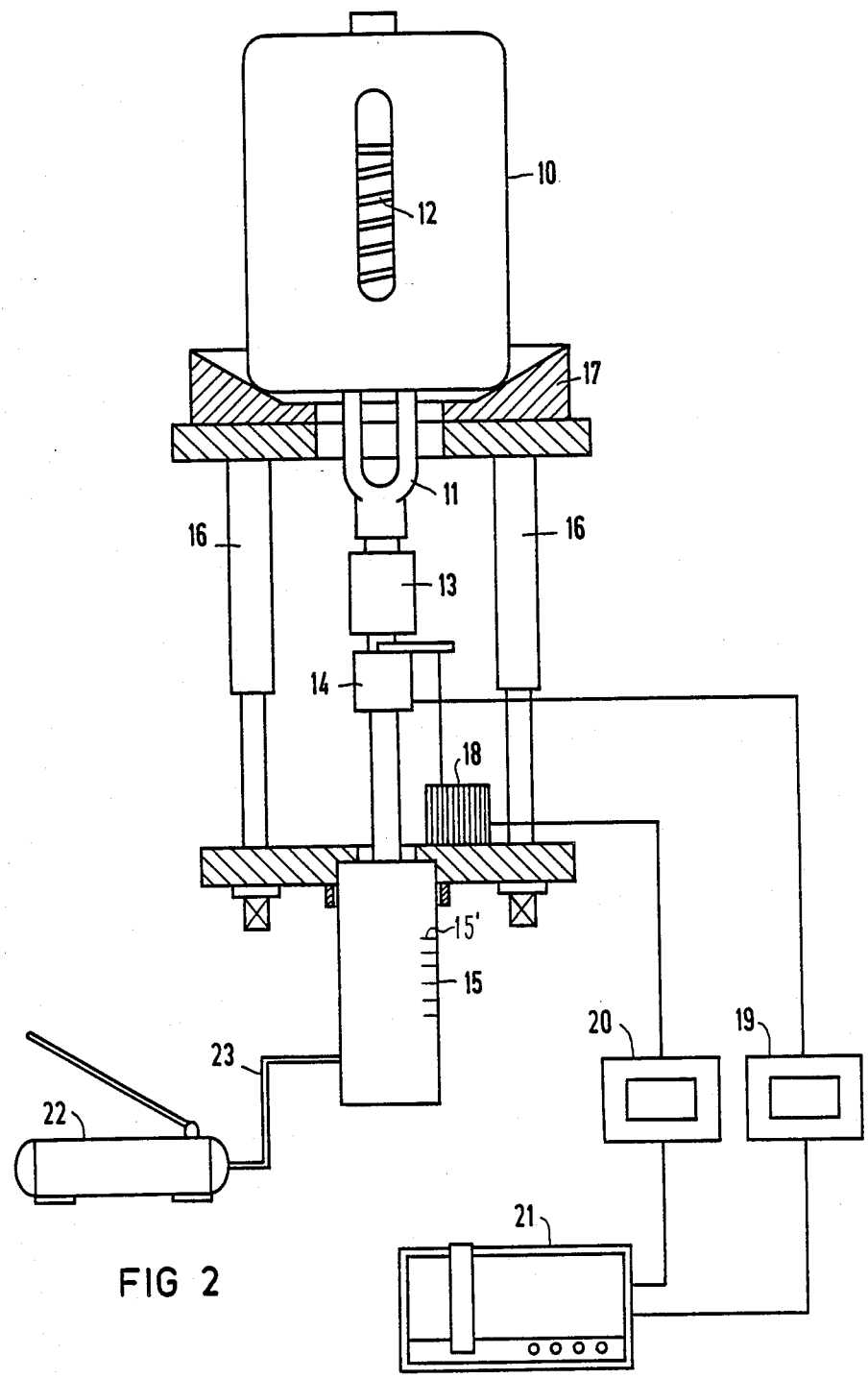

FIG. 1 is a diagrammatic, cross-sectional view of a constant support hanger, which is connected to an apparatus for performing the method according to the invention, instead of to a pipe: and FIG. 2 is a more detailed cross-sectional view of a suspension device connected to an apparatus for performing the method according to the invention which is illustrated in a schematic circuit diagram.

Referring now to the figures of the drawings in detail and first, particularly, to FIG. 1 thereof, there is seen a constant support hanger 1 having a device 2 for securing it to a building structure and a further device 3 on which a pipe run or pipeline is held. Inner or middle and outer mechanical springs 4, 5 and 6 are located in the constant support hanger 1. The outer springs 5 and 6 are each connected to the inner spring 4. The device 3 for holding a pipe run is connected to the middle spring 4. In order to perform functional testing of the constant support hanger 1, the device 3 for holding a pipe run is connected to a conventional hydraulic cylinder 7, instead of to a pipe run. The pipe may be held by other devices, such as a hanger or support as shown in U.S. Pat. Nos. 3,102,706 and 3,588,010, during testing. The hydraulic cylinder 7 has a connection 8 for a hydraulic pump and connections 9 for pressure pickups. A non-illustrated piston which is located in the hydraulic cylinder 7, is moved by medium fed into the cylinder and is connected to the device 3 of the constant support hanger 1. The springs 4-6 are stretched by a movement of the piston. The displacement travel can be read off markings 7' on the hydraulic cylinder 7. The pressure in the hydraulic cylinder 7 and thus the force upon the device 3 of the constant support hanger 1 is ascertained by pressure pickups. The spring constant can be derived from the ascertained values and the instantaneous value of the spring constant provides an indication of the functional capacity of the constant support hanger 1.

A suspension device 10 as shown in FIG. 2 is a spring hanger comprising a device 11 for holding a pipe run. A spring 12 is located in the suspension device 10. In order to perform functional testing of the suspension device 10, the device 11 for holding a pipe run is connected through a threaded sleeve 13 and a force measuring instrument 14 to a hydraulic cylinder 15 has measuring points or markings 15' thereon and, instead of to a pipe run. The hydraulic cylinder 15 is held in the housing of a clamping device 16. The clamping device 16 is supported on the housing of the suspension device 10 through a conical adaptor washer 17. Disposed on the clamping device 16 is a travel pickup 18, which is connected to the device 11 for holding a load. To this end, the travel pickup 18 is connected between the threaded sleeve 13 and the force measuring instrument 14. The force measuring instrument 14 and the travel pickup 18 are connected through measurement amplifiers 19 and 20 to an evaluation unit 21. A hydraulic pump 22 is connected to the hydraulic cylinder 15 through a hydraulic hose 23.

We claim:

1. In combination with a suspension device such as a spring hanger or a constant support hanger holding a pipe run on a building structure and having at least one mechanical spring, a method for functional testing of the suspension device for a load, which comprises releasing the load from the suspension device, holding the load with other devices, connecting a hydraulic device to the suspension device to be tested instead of the load for stretching the spring of the suspension device without removing the spring from the suspension device, and ascertaining and recording the pressure necessary for stretching the spring and therefore the spring constant of the spring based on the operating travel of the spring, with a pressure pickup and a recorder connected to the hydraulic device.

2. In combination with a suspension device holding a pipe run on a building structure and having at least one mechanical spring, an apparatus for functional testing of the suspension device for a load, comprising a hydraulic device connected to the suspension device to be tested instead of the load for stretching the spring of the suspension device, the spring being disposed within the suspension device said hydraulic device having a plurality of measuring points, and a pressure pickup and a recorder connected to said hydraulic device for determining and recording the pressure necessary for stretching the spring and therefore the spring constant of the spring in the suspension device based on the operating travel of the spring.

3. Apparatus according to claim 2, including a hydraulic pump connected to said hydraulic device.

4. Apparatus according to claim 2, wherein the suspension device to be tested has a housing, and including a clamping device connected to the suspension device to be tested and supported on the housing of the suspension device, said hydraulic device including a hydraulic cylinder having a housing held in said clamping device, a device connected to said hydraulic cylinder for holding a load with the suspension device, a force measuring instrument disposed between said device for holding a load and said hydraulic cylinder, an evaluation unit electrically connected to said force measuring instrument, and a travel pickup connected to said clamping device, connected to said device for holding a load and electrically connected to said evaluation unit.

5. Apparatus according to claim 4, including a conical adaptor washer disposed between the housing of the suspension device to be tested and said clamping device.

6. Apparatus according to claim 4, including a threaded sleeve mechanically connecting said device for holding a load to said hydraulic cylinder.

7. Apparatus according to claim 2, wherein the suspension device is a spring hanger.

8. Apparatus according to claim 2, wherein the suspension device is a constant support hanger.

* * * * *